United States Patent
Schütte et al.

(10) Patent No.: US 6,323,349 B2
(45) Date of Patent: Nov. 27, 2001

(54) METHOD OF PRODUCING EXPOXIDES IN THE GASEOUS PHASE

(75) Inventors: Rüdiger Schütte, Alzenau; Georg Markowz, Karlstein; Peter Esser, Recklinghausen; Torsten Balduf; Georg Thiele, both of Hanau; Steffen Hasenzahl, Maintal, all of (DE)

(73) Assignee: Degussa-Huls Aktiengesellschaft, Frankfurt am Main (DE)

( * ) Notice: Subject to any disclaimer, the term of this patent is extended or adjusted under 35 U.S.C. 154(b) by 0 days.

(21) Appl. No.: 09/764,140

(22) Filed: Jan. 19, 2001

(30) Foreign Application Priority Data

Jan. 21, 2000 (DE) .............................. 100 02 514

(51) Int. Cl.$^7$ ................................. C07D 301/12
(52) U.S. Cl. ............................ 549/523; 549/531
(58) Field of Search ...................... 549/523, 531

(56) References Cited

U.S. PATENT DOCUMENTS

| | | | |
|---|---|---|---|
| 4,374,260 | 2/1983 | Cavitt | 549/534 |
| 5,874,596 | 2/1999 | Onozawa et al. | 549/531 |
| 6,106,803 | 8/2000 | Hasenzahl et al. | 423/705 |

FOREIGN PATENT DOCUMENTS

| | | |
|---|---|---|
| 2206626 | 11/1998 | (CA) . |
| 197 31 627 | 1/1999 | (DE) . |

OTHER PUBLICATIONS

116:60020e, Nagiev, et al., "Gas–phase oxidation of propylene by hydrogen peroxide," Chemical Abstracts, vol. 116, No. 8, Feb. 24, 1992, p. 60012.

102: 132503a, Guseinov et al., "Mechanisms of synthesis of oxygen–containing monomers on solid catalysts," Chemical Abstracts, vol. 102, No. 16, Apr. 22, 1985, p. 132500.

95:219918a, Nagiev et al., "Gas–phase cooxidation of lower olefins by hydrogen peroxide," Chemical Abstracts, vol. 95, No. 25, Dec. 21, 1981, p. 499.

*Primary Examiner*—Ba K. Trinh
(74) *Attorney, Agent, or Firm*—Pillsbury Winthrop LLP

(57) ABSTRACT

A method for epoxidation of olefins with 2 to 6 C atoms, especially propene, with hydrogen peroxide in the gas phase at a temperature below 250° C. The reaction is carried out by bringing a gas mixture containing the olefin, hydrogen peroxide and water into contact with the catalyst from the series of compounds of an element of the 4th to the 6th subgroup of the periodic table or of arsenic or selenium and molecular sieves in the absence of a liquid phase. Titanium-containing molecular sleeves are preferred catalysts.

13 Claims, No Drawings

METHOD OF PRODUCING EPOXIDES IN THE GASEOUS PHASE

This application claims priority from German Application No. 100 02 514.5, filed on Jan. 21, 2000, the content of which is hereby incorporated here by reference.

BACKGROUND OF THE INVENTION

1. Field of the Invention

The invention relates to a method of producing epoxides [oxiranes; literally "olefin oxides"] with 2 to 6 C atoms, especially propene oxide, by gas-phase epoxidation of the corresponding olefin with 2 to 6 C atoms with hydrogen peroxide in the presence of a solid catalyst.

2. Background Information

The epoxidation of olefins such as propene using hydrogen peroxide is successful in the liquid phase using a titanium silicalite catalyst—see U.S. Pat. No. 5,874,596 and DE 197 31 627. A disadvantage of this method is the rapid deactivation of the catalyst by high-boiling byproducts.

The liquid-phase epoxidation of olefins with hydrogen peroxide in the presence of a catalyst containing molybdenum or tungsten is also known—see Weigert et al., Chem.-Ztg. [German=Chemische Zeitung] 99, 19 (1975). The workup of the reaction mixture and the recovery of the catalyst are quite expensive.

The carrying out of the epoxidation in a membrane reactor is also known from CA 2,206,626 A1, in which catalytically active particles are intercalated [inserted] in the composite membrane and a gas phase with the olefin such as propene to be epoxidized is located on the one side of the membrane and on the other side a liquid phase with hydrogen peroxide is located. The catalytically active particles preferably consist of titanium silicalite.

Instead of in the liquid phase, ethylene can also be epoxidized in the gas phase in the presence of a silver-containing catalyst at 200 to 300° C. In this instance, air or molecular oxygen is used as epoxidizing agent instead of hydrogen peroxide (see, e.g., U.S. Pat. No. 4,374,260).

The attempt has also been made to epoxidize lower olefins with hydrogen peroxide in the gas phase, during which hydrogen peroxide is thermally or catalytically activated: Thus, according to G. M. Mamedjarov and T. M. Nagiev (Azerb. Khim. Zh. [Russian=Azerbaizhanskii Khimicheski Zhurnal] ethene and propene can be epoxidized at 500 to 600° C. in a gas phase in the absence of a catalyst. Epoxide yields, that were initially low, were able to be increased by T. M. Nagiev et al. (Neftekhimiya [Russian] 31 (1991), 670–675) by optimization to approximately 50 to 55%. The high reaction temperatures, that oppose an economic process, are disadvantageous.

H. M. Gusenov et al. (Azerb. Khim. Zh. (1984), 47–51) investigated the mechanism of a similar method; however, the gas-phase epoxidation takes place here in the presence of a Si-containing catalyst at 425 to 500° C. Propene and vaporous hydrogen peroxide are supplied to a tubular reactor; the conversion of propene is in a range of 15 to 65%.

T. M. Nagiev et al. (Neftekhimiya 31, (1991), 670–675) teach an improved gas-phase epoxidation in the presence of an Fe-containing catalyst: Propene is epoxidized with hydrogen peroxide to propene oxide using magnetite as catalyst at approximately 250° C. with a yield of about 30%. However, the catalytic service life of 25 h is very low. A longer service life and a further lowering of the reaction temperatures can be obtained with an $Fe^{III}OH$-protoporphyrin catalyst bound to aluminum oxide as carrier. A propene oxide yield of approximately 50% is obtained with this catalyst at a temperature of about 160° C. and a molar dosing ratio of $C_3H_6:H_2O_2:H_2O=1:0, 2:0,0.8$.

SUMMARY OF THE INVENTION

It is an object of the invention to provide a further method for the catalytic gas-phase epoxidation of lower olefins with hydrogen peroxide in which the catalyst should be iron-free (non-ferrous) and wherein the epoxidation can be carried out below 250° C. The term "iron-free" does not exclude here the presence of traces of iron in the catalyst within the scope of customary impurities.

This object is accomplished by a method of producing an epoxide with 2 to 6 C atoms, especially propylene oxide, by gas-phase epoxidation of the olefin to be epoxidized with hydrogen peroxide, comprising bringing the a gaseous mixture containing the olefin, hydrogen peroxide and water into contact with a solid catalyst and the isolating of the epoxide from the reaction mixture, that is characterized in that a compound of an element of the 4th to the 6th subgroup of the periodic table of the elements or arsenic or selenium or a molecular sieve is used as catalyst and the epoxidation is carried out at a temperature below 250° C. in the absence of a liquid phase.

The subclaims are directed to preferred embodiments of the method of the invention.

One class of suitable catalyst concerns molecular sieves, especially synthetic zeolites. An especially preferred catalyst from the family of molecular sieves is based on titanium-containing molecular sieves of the general formula $(SiO_2)_{1-x}(TiO_2)_x$ such as titanium silicalite-1 (TS-1) with MFI crystalline structure, titanium silicalite-2 (TS-2) with MEL crystalline structure, titanium beta zeolite with BEA crystalline structure and titanium silicalite-48 with the crystalline structure of zeolite ZSM 48. The $TiO_2$ content in TS-1 is preferably in a range of 2 to 4%. Titanium silicates are commercially obtainable. Instead of pure titanium silicates combination products can be used that also contain amorphous or crystalline oxides such as $SiO_2$, $TiO_2$, $Al_2O_3$, $ZrO_2$ in addition to titanium silicate. Crystallites of titanium silicate can be homogeneously distributed in this instance with the crystallites of the other oxides and form granulates or can be located as the outer shell on a core of other oxides.

Another class of catalysts to be used in accordance with the invention preferably concerns inorganic, especially oxidic compounds containing as catalytically active element one or more elements of the 4th to the 6th subgroup of the periodic table or an arsenic compound or selenium compound. Compounds of titanium, zirconium, vanadium, niobium, tantalum, chromium, molybdenum and tungsten are preferably concerned. The catalytic action is viewed in the fact that, without excluding other mechanisms, hydrogen peroxide is activated by the porous structure of the catalyst and/or the enabling of the catalyst to the reversible formation of peroxo compounds.

Examples of suitable catalysts are vanadium oxides, vanadates, niobium oxide and tantalum oxide and —oxide hydrates as well as $H_2O_2$ adducts of the cited oxides and oxide hydrates.

Another especially suitable class of epoxidation catalysts contains molybdenum or tungsten. Examples are $MoO_3$ and $WO_3$, molybdic- and tungstic acids, alkali- and alkaline-earth molybdates and —tungstates in is far as their basicity does not result in a hydrolysis of the epoxide, homo- and heteropolymolybdates and tungstates (=homo-and heteropolyacids) and $H_2O_2$ adducts of the cited substance classes such as peroxomolybdic acid, peroxotungstic acid, peroxomolybdates and peroxotungstates that can also be formed in situ during the epoxidation from other Mo and W compounds.

The catalyst is usually particulate; however, the active component can be fixed to the walls of a monolithic carrier with through tubes or slots. Catalysts in granulate, spherical or rod-like form are used with particular advantage. Particulate catalysts can be used in the form of a fixed-bed charge or in the form of a fluid bed.

A gaseous mixture containing an olefin, hydrogen peroxide, water and optionally another gas for rendering inert is passed thereby through the catalytic charge [packing] or is used as a fluid-bed gas. The method can be carried out batchwise or continuously. It is essential that no liquid phase develops during the epoxidation in the reactor that is, on the catalyst. This increases the catalytic service life and reduces the expense of a regeneration.

It can be advantageous, if required, in particular in order to adjust isothermal reaction conditions and to avoid/reduce therewith the formation of high-boiling byproducts, to dilute the catalytic material uniformly or in lamellar fashion with an inert or not very active material. Examples of suitable diluting agents are glass powder or glass spheres [bulbs, marbles], aluminum oxide, silicon dioxide and particulate mineral and/or silicatic substances. Hotspots are avoided by carrying out an isothermal reaction, which has an advantageous effect on the service life of the catalyst.

In addition to the co-use of an essentially inert fixed-bed material it can be advantageous to mix an inert gas into the gas containing the olefin to be epoxidized. Suitable inert gases are, for example, nitrogen, noble gases and lower alkanes. The amount of inert gas to be used is a function of the desired reaction temperature. In order to control the catalytic activity and/or to modify the reaction conditions other gases such as low-boiling, organic solvents or ammonia can also be added alternatively or additionally to the use of inert gases.

Gaseous hydrogen peroxide is used for the epoxidation that is advantageously obtained from an aqueous hydrogen peroxide solution, in particular one with 30 to 90% by weight hydrogen peroxide by evaporation in an apparatus suitable to this end. In order to avoid subsequent reactions of the formed epoxide with the water originating from the evaporation of aqueous hydrogen peroxide and formed during the epoxidation from $H_2O_2$, preferably highly concentrated $H_2O_2$ solutions are supplied to the evaporator. This also reduces the expenditure of energy. The main resultant product is 1.2-propene diol. The $H_2O_2$ content in the gaseous mixture is limited by the vapor pressure at the reaction temperature and is preferably 0.01 to 25% by volume, preferably 0.1 to 15% by volume.

The olefin to be epoxidized can be used in any ratio to the hydrogen peroxide. An at least equimolar amount, especially preferably an excess of olefin is preferred. The molar dosing ratio of olefin to $H_2O_2$ is preferably in a range of greater than 1 to 1 up to 2 to 1.

The olefin to be epoxidized contains 2 to 6 C atoms and is therefore ethene, propene, 1-butene, 2-butene, isobutene as well as pentanes and hexenes including cyclohexene and cyclopentene. The method is especially preferably suited for the production of propene oxide from propene.

The epoxidation is carried out at a temperature below 250° C., preferably at a temperature and a range of 20 to 200° C., and especially preferably in a range of 60 to 150° C. The epoxidation preferably takes place in a pressure range of 1 kPa to 2 MPa, preferably 10 kPa to 1 MPa and especially preferably 20 kPa to 400 kPa.

The workup of the reaction mixture takes place in a manner known to an expert in the art, for example, by condensation of the epoxide and the separation of the epoxide from the other gases or by a gas washer [scrubber]. Non-reacted olefin can be recycled.

Known membrane separation methods such as gas permeation methods, vapor permeation methods and pervaporation methods are also suitable for working up the reaction mixture, that includes a separation of the epoxide from the non-reacted olefin as well as from gas mixtures and condensates obtained by a partial condensation. Membranes based on polymers and molecular sieves can be considered as membrane.

The method in accordance with the invention is characterized by the simple carrying out of the reaction and the low reaction temperature. Different catalysts can be used, wherewith the reaction [conversion] can also be optimized in this respect. The catalysts have a long service life on account of the mild reaction conditions.

DETAILED DESCRIPTION OF THE INVENTION

All tests were carried out in a glass apparatus consisting of an evaporator, an externally heated tubular reactor, a cooled gas scrubber (ethyl acetate or MTBE as solvent) and of a low-temperature condenser. Commercial, stabilized hydrogen peroxide solutions and titanium silicate TS-1 were used. The measuring and dosing of the gas currents (propene, nitrogen) and of the hydrogen peroxide solution took place with mass flowthrough sensors of the Bronkhorst company.

EXAMPLE 1

5 g/h of a 50% by weight hydrogen peroxide solution and a gas mixture of 2.8 Nl/h propene and 20 Nl/h nitrogen preheated to the evaporation temperature were dosed into the evaporator (100° C.). The gas mixture exiting out of the evaporator was passed in the reactor over a catalytic bed of 10 g TS-1 and 10 g glass spheres. The molar dosing ratio was 1.7 moles propene per mole hydrogen peroxide. A hydrogen peroxide conversion of 100%, a propene conversion of 25% and a propene oxide yield relative to converted propene of 30% were achieved. Propane diol, hydroxyacetone, propanal, propionic acid, acetic acid, formic acid and formaldehyde are identified as byproducts.

EXAMPLE 2

5 g/h of a 50% by weight hydrogen peroxide solution and a gas mixture of 1.7 Nl/h propene and 21.1 Nl/h nitrogen preheated to the evaporation temperature were dosed into the evaporator (100° C.). The gas mixture exiting out of the evaporator was passed in the reactor over a catalytic bed of 10 g TS-1 and 10 g glass spheres. The molar ratio of propene:$H_2O_2$=1:1. The hydrogen peroxide conversion was 100%, the propene conversion 30% and the yield of propene oxide relative to the reacted propene was 23%. Propane diol, hydroxyacetone, propanal, propionic acid, acetic acid, formic acid and formaldehyde are identified as byproducts.

What is claimed is:

1. A method of producing an epoxide with 2 to 6 C atoms, especially propylene oxide, by gas-phase epoxidation of the olefin to be epoxidized with hydrogen peroxide, comprising bringing a gaseous mixture containing the olefin, hydrogen peroxide and water into contact with a solid catalyst and the isolating of the epoxide from the reaction mixture, characterized in that a compound of an element of the 4th to the 6th subgroup of the periodic table of the elements or arsenic or selenium or a molecular sieve is used as catalyst and the epoxidation is carried out at a temperature below 250° C. in the absence of a liquid phase.

2. The method according to claim 1, wherein a titanium-containing zeolite, especially titanium silicalite-1 (TS-1) with a $TiO_2$ content in a range of 2 to 4% is used as catalyst.

3. The method according to claim 1, wherein an oxidic compound of vanadium, niobium, tantalum or a molybdenum compound or tungsten compound from the series of the oxides, acids, molybdates, tungstates, molybdenum-containing or tungsten-containing homo- or heteropolyacids and $H_2O_2$ adducts of these classes is used as catalyst.

4. The method according to one of claims 1 to 3, wherein the gas mixture is passed through a fixed bed of particulate catalyst.

5. The method according to claim 4, wherein the fixed bed additionally contains substantially inert, particulate solids.

6. The method according to one of claims 1 to 3, wherein the gas mixture is brought into contact with the catalyst at a temperature in the range of 60 to 150° C.

7. The method according to claim 6, wherein the fixed bed additionally contains substantially inert, particulate solids.

8. The method according to claim 7, wherein the fixed bed additionally contains substantially inert, particulate solids.

9. The method according to one of claims 1 to 3, wherein a gas mixture consisting of the olefin to be epoxidized, of hydrogen peroxide, water and at least one inert gas from the series of nitrogen, $C_1$ to $C_4$ alkanes and noble gases is brought into contact with the catalyst.

10. The method according to one of claims 1 to 3, wherein the gas mixture to be brought into contact with the catalyst is produced by evaporating an aqueous hydrogen peroxide solution and feeding in the olefin and, if required, an inert gas.

11. The method according to one of claims 1 to 3, wherein the gas mixture to be brought into contact with the catalyst contains the olefin and hydrogen peroxide in a molar ratio in a range of greater than 1 to 1 up to 5 to 1.

12. The method according to one of claims 1 to 3, wherein the gas mixture is brought into contact with the catalyst at a pressure in a range of 10 kPa to 1 MPa.

13. The method according to one of claims 1 to 3, wherein the reaction mixture or gas mixtures obtained after a partial condensation of said reaction mixture are worked up using a membrane separating method.

* * * * *